United States Patent
Fujioka et al.

(10) Patent No.: US 12,144,622 B2
(45) Date of Patent: Nov. 19, 2024

(54) ENZYME SENSOR AND ENZYME SENSOR SYSTEM

(71) Applicant: JSR Corporation, Minato-ku (JP)

(72) Inventors: Masayasu Fujioka, Minato-ku (JP); Akinori Ito, Minato-ku (JP); Kenichi Hamada, Minato-ku (JP)

(73) Assignee: JSR Corporation, Minato-ku (JP)

( * ) Notice: Subject to any disclaimer, the term of this patent is extended or adjusted under 35 U.S.C. 154(b) by 596 days.

(21) Appl. No.: 16/346,734

(22) PCT Filed: Nov. 7, 2017

(86) PCT No.: PCT/JP2017/040094
§ 371 (c)(1),
(2) Date: May 1, 2019

(87) PCT Pub. No.: WO2018/088391
PCT Pub. Date: May 17, 2018

(65) Prior Publication Data
US 2020/0054252 A1    Feb. 20, 2020

(30) Foreign Application Priority Data

Nov. 8, 2016   (JP) ................................. 2016-218104

(51) Int. Cl.
*A61B 5/1486*    (2006.01)
*A61B 5/145*    (2006.01)
(Continued)

(52) U.S. Cl.
CPC ........ *A61B 5/1486* (2013.01); *A61B 5/14517* (2013.01); *C12Q 1/005* (2013.01);
(Continued)

(58) Field of Classification Search
CPC ........ C12Q 1/006; C12Q 1/005; C12Q 1/001; C12Q 1/26; C12Q 1/002; C12Q 1/54;
(Continued)

(56) References Cited

U.S. PATENT DOCUMENTS 7,034,164 B1 * 4/2006 Cosnier ................ G01N 33/545
548/562
2005/0215871 A1 * 9/2005 Feldman ................ C12Q 1/002
204/403.01
(Continued)

FOREIGN PATENT DOCUMENTS

JP    2000-81409 A    3/2000
JP    2004-294231 A    10/2004
(Continued)

OTHER PUBLICATIONS

International Search Report issued Jan. 23, 2018 in PCT/JP2017/040094 filed on Nov. 7, 2017.
(Continued)

*Primary Examiner* — Carrie R Dorna
*Assistant Examiner* — Karen E Toth
(74) *Attorney, Agent, or Firm* — Oblon, McClelland, Maier & Neustadt, L.L.P.

(57) ABSTRACT

An enzyme sensor is configured to measure a measurement target substance included in a secretion of a living body. The enzyme sensor includes a layered structure including (a) an absorber layer configured to absorb the secretion, (b) an enzyme layer containing an enzyme, and (c) an electrode part arranged in an order of the (a), the (b), and the (c). The absorber layer includes a polymeric material having a chemically bound crosslinked structure.

10 Claims, 5 Drawing Sheets

(51) Int. Cl.
  *C12Q 1/00*    (2006.01)
  *G01N 27/327*  (2006.01)
  *G01N 27/416*  (2006.01)
  *G06F 9/06*    (2006.01)
  *G06F 15/00*   (2006.01)
(52) U.S. Cl.
  CPC ....... *G01N 27/327* (2013.01); *G01N 27/3277* (2013.01); *G01N 27/416* (2013.01); *G01N 27/3272* (2013.01); *G01N 2333/904* (2013.01); *G06F 9/06* (2013.01); *G06F 15/00* (2013.01)
(58) Field of Classification Search
  CPC .............. A61B 5/1486; A61B 5/14735; G01N 27/3271; G01N 27/327; G01N 27/3277; G01N 27/4145; G01N 2333/902; G01N 2333/904
  See application file for complete search history.

(56) References Cited

U.S. PATENT DOCUMENTS

| | | | |
|---|---|---|---|
| 2006/0042944 A1* | 3/2006 | Rodgers | C12Q 1/004 204/403.09 |
| 2008/0027287 A1 | 1/2008 | Shah et al. | |
| 2008/0002939 A1 | 2/2008 | Roche et al. | |
| 2008/0114228 A1* | 5/2008 | McCluskey | A61B 5/14865 340/539.12 |
| 2011/0065126 A1* | 3/2011 | Ito | G01N 33/553 436/71 |
| 2012/0028283 A1 | 2/2012 | Hoss et al. | |
| 2012/0186997 A1 | 7/2012 | Li et al. | |
| 2013/0053668 A1 | 2/2013 | Lin | |
| 2015/0313520 A1 | 11/2015 | Hoss et al. | |
| 2016/0157765 A1* | 6/2016 | Zhu | C08L 83/12 600/347 |
| 2016/0235365 A1* | 8/2016 | Liu | A61B 5/1473 |
| 2017/0258377 A1 | 9/2017 | Hoss et al. | |
| 2018/0256083 A1 | 9/2018 | Hoss et al. | |

FOREIGN PATENT DOCUMENTS

| | | |
|---|---|---|
| JP | 2009-528083 A | 8/2009 |
| JP | 2009-244014 A | 10/2009 |
| JP | 2009-544409 A | 12/2009 |
| JP | 2014-503080 A | 2/2014 |
| WO | WO 2012/100130 A1 | 7/2012 |

OTHER PUBLICATIONS

Written Opinion (PCT/ISA/237) issued Jan. 23, 2018 in PCT/JP2017/040094 filed on Nov. 7, 2017.
Gao, W. et al., "Fully integrated wearable sensor arrays for multiplexed in situ perspiration analysis," Nature, vol. 529, Jan. 2016 (Total 18 pages).
Jia, W. et al., "Electrochemical Tattoo Biosensors for Real-Time Noninvasive Lactate Monitoring in Human Perspiration," American Chemical Society, Analytical Chemistry, vol. 85, 2013, pp. 6553-6560.
Notice of Reasons for Refusal issued Feb. 2, 2021 in Japanese Patent Application No. 2018-550209 (with English language translation), 6 pages.
Japanese Office Action issued Apr. 13, 2021 in Japanese Patent Application No. 2018-550209 (with unedited computer generated English translation), 8 pages.
International Search Report and Written Opinion issued Jan. 23, 2018 in PCT/JP2017/040094 (reference previously filed, now submitted with English translation of the Search Report), 8 pages.
Extended European Search Report issued Jun. 19, 2020 in European Patent Application No. 17870095.1, 7 pages.
International Preliminary Report on Patentability and Written Opinion issued May 23, 2019 in PCT/JP2017/040094 (submitting English translation only), 7 pages.
Office Action issued Oct. 21, 2022 in European Patent Application No. 17870095.1, filed Nov. 7, 2017, 5 pages.
Office Action issued Jul. 16, 2024 in European Patent Application No. 17870095.1.

* cited by examiner

ENZYME SENSOR AND ENZYME SENSOR SYSTEM

CROSS-REFERENCE TO RELATED APPLICATION

This international application claims the benefit of Japanese Patent Application No. 2016-218104, filed on Nov. 8, 2016 in the Japan Patent Office, and the entire disclosure of Japanese Patent Application No. 2016-218104 is incorporated herein by reference.

TECHNICAL FIELD

The present disclosure relates to an enzyme sensor and an enzyme sensor system.

BACKGROUND ART

Enzyme sensors that measure measurement target substances contained in secretions of living bodies are conventionally known. The enzyme sensor comprises an absorber layer enabled to absorb the secretions, an enzyme layer containing an enzyme, and an electrode part. The enzyme sensor detects, with the electrode part, electrode-detectable substances generated from the measurement target substance in the presence of the enzyme (see Non-patent Documents 1 and 2).

PRIOR ART DOCUMENTS

Non-Patent Documents

Non-patent Document 1: Wei Gao et al. (Nature, Vol. 529, 509- (2016))
Non-patent Document 2: Wenzhao Jia et al. (Anal. Chem., Vol. 85, 6553-6560 (2013))

SUMMARY OF THE INVENTION

Problems to be Solved by the Invention

Detection sensitivity of the conventional enzyme sensor is prone to decrease when a measurement time is long. Preferably, one aspect of the present disclosure provides an enzyme sensor and an enzyme sensor system that are less prone to have their detection sensitivity decreased when a measurement is continued for a long time.

Means for Solving the Problems

One aspect of the present disclosure is an enzyme sensor configured to measure a measurement target substance contained in a secretion of a living body. The enzyme sensor comprises a layered structure comprising (a) an absorber layer configured to absorb the secretion, (b) an enzyme layer containing an enzyme, and (c) an electrode part arranged in the order of (a), (b), and (c). The absorber layer comprises a polymeric material having a chemically bound crosslinked structure.

The enzyme sensor in one aspect of the present disclosure is not prone to have its detection sensitivity decreased when a measurement is carried out for a long time. The reason for this, at least partially, is assumed to be that the absorber layer comprises a polymeric material having a chemically bound crosslinked structure.

MODE FOR CARRYING OUT THE INVENTION

Example embodiments of the present disclosure will be described hereinafter with reference to the drawings.

FIRST EMBODIMENT

1. Structure of Enzyme Sensor 1

Figure 1:
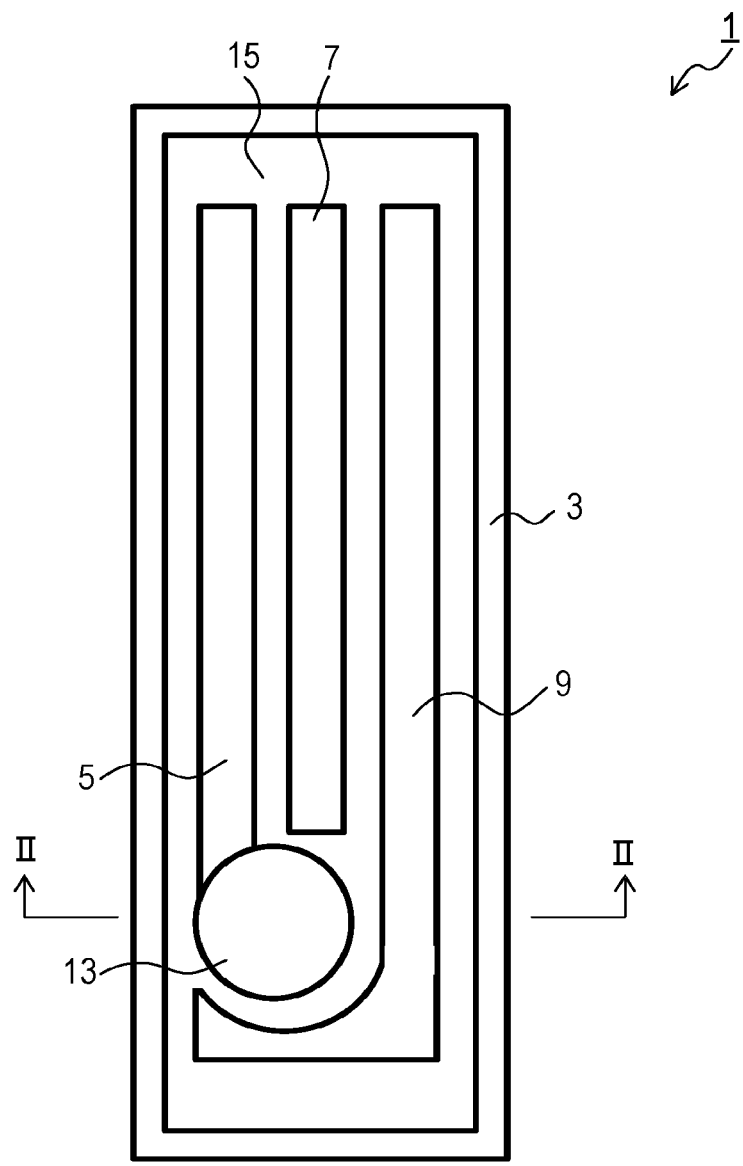
FIG. 1 is a top view showing a configuration of an enzyme sensor.
Figure 2:
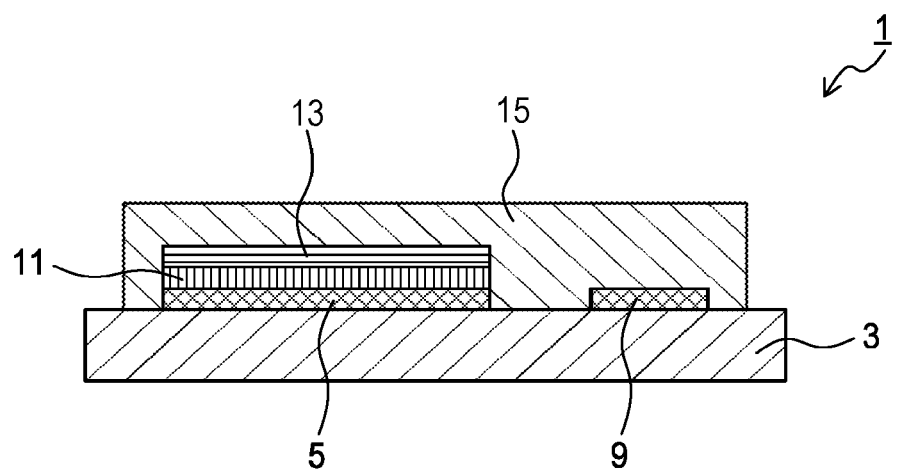
FIG. 2 is a cross sectional view taken along line II-II in FIG. 1.

Referring to FIG. 1 and FIG. 2, hereinafter is a description of a structure of an enzyme sensor 1. The enzyme sensor 1 measures a measurement target substance contained in a secretion of a living body. The enzyme sensor 1 comprises a base material layer 3, a working electrode 5, a reference electrode 7, a counter electrode 9, an electron transport mediator layer 11, an enzyme layer 13, and an absorber layer 15. The secretion of the living body may be perspiration, tears, saliva, urine, and so on. The measurement target substance contained in the secretion of the living body may be lactic acid, glucose (grape sugar), ethanol, uric acid, urea, vitamins, free cholesterol, phosphate ion, and so on.

The base material layer 3 supports the working electrode 5, the reference electrode 7, and the counter electrode 9. As long as the working electrode 5, the reference electrode 7, and the counter electrode 9 are supported, the base material layer 3 is not limited to a particular base material layer. Examples of a material for the base material layer 3 may include thermoplastic elastomers such as thermoplastic styrene-based elastomer, thermoplastic olefin-based elastomer, thermoplastic diene-based elastomer, thermoplastic vinyl chloride-based elastomer, thermoplastic urethane-based elastomer, and thermoplastic silicone-based elastomer; and thermoplastic resins such as polyethylene, polypropylene, polystyrene, polyethylene terephthalate, cellulose, acrylonitrile-styrene (AS) resin, glass epoxy, acrylonitrile-butadiene-styrene (ABS) resin, methacrylic resin, and vinyl chloride. Among these, a thermoplastic elastomer is preferably used due to its excellent flexibility. Thickness of the base material layer 3 is preferably 5 μm or greater, more preferably 20 μm or greater, and yet more preferably 50 μm or greater. The thickness of the base material layer 3 is preferably 2 mm or less, more preferably 1 mm or less, and yet more preferably 500 μm or less. The material layer 3 is superior in supporting property and flexibility when the thickness of the base material layer 3 is within the aforementioned ranges.

The working electrode 5, the reference electrode 7, and the counter electrode 9 correspond to the electrode part. The working electrode 5, the electron transport mediator layer 11, the enzyme layer 13, and the absorber layer 15 are layered in this order and arranged on the base material layer 3. Shapes of the working electrode 5, the reference electrode 7, and the counter electrode 9 are, for example, circular such as a true circle and an ellipse, or multangular such as a triangle and a quadrangle. Diameters of the working electrode 5, the reference electrode 7, and the counter electrode 9 are, for example, 1 mm or greater and 5 cm or less when viewed from a direction orthogonal to the base material layer 3.

The electron transport mediator layer 11 comprises an electron transport mediator. Examples of the electron transport mediator include ferrocene, quinones, ferrocenecarboxylic acid, potassium ferricyanide, osmium complex, ruthenium complex, phenothiazine derivative, phenazine methosulfate derivative, p-aminophenol, meldola blue, and 2,6-dichlorophenolindophenol.

The enzyme layer 13 contains an enzyme. Examples of the enzyme include lactate oxidase (lactic acid oxidizing enzyme), glucose oxidase (glucose oxidizing enzyme), alkaline phosphatase, alcohol oxidase, uricase, L-amino-acid oxidase, urease, cholesterol oxidase, phosphatase, and horse radish peroxidase.

The absorber layer 15 covers the working electrode 5, the electron transport mediator layer 11, the enzyme layer 13, the reference electrode 7, and the counter electrode 9. The absorber layer 15 is made from a hydrogel having a chemically bound crosslinked structure. The absorber layer 15 is positioned to be in contact with the living body when the enzyme sensor 1 is in use.

The absorber layer 15 has an ability to absorb the secretion of the living body. With reference to JIS7209, the lower limit of the water absorption ratio of the absorber layer 15 is preferably 10% or greater, more preferably 30% or greater, yet more preferably 50% or greater, still more preferably 100% or greater, and particularly preferably 500% or greater. With reference to JIS7209, the upper limit of the water absorption ratio of the absorber layer 15 is preferably 100,000% or less, more preferably 50,000% or less, yet more preferably 10,000% or less, and particularly preferably 5,000% or less. The enzyme sensor is superior in sensitivity, stability, and durability when the water absorption ratio is within the aforementioned ranges.

The enzyme sensor 1 may be attachable to the living body, or may be other type of sensor. Examples of the living body include human, and animals other than human. Preferably, the absorber layer 15 contacts the living body when the enzyme sensor 1 is attached to the living body. A part of the living body the enzyme sensor 1 is attached to may be appropriately determined and may include, for example, wrist, leg, head, chest, and abdomen.

2. Method of Producing Enzyme Sensor 1

The enzyme sensor 1 can be produced by the following method for example. A material for electrode formation is applied on the base material layer 3 by screen printing to form the working electrode 5, the reference electrode 7, and the counter electrode 9. The material for electrode formation to form the working electrode 5 and the counter electrode 9 may include a material that contains a carbon material such as carbon, carbon nanotube, fullerene, and graphene. The material for electrode formation to form the reference electrode 7 may include a material that contains silver and silver chloride.

Next, a material for electron transport mediator layer formation is applied on the working electrode 5 and dried at room temperature to form the electron transport mediator layer 11. Examples of the material for electron transport mediator layer formation may include a solution that contains the electron transport mediator.

Next, a material for enzyme layer formation is applied on the electron transport mediator layer 11 and dried at room temperature to form the enzyme layer 13. Thus formed enzyme layer may contain a polymeric material having a chemically bound crosslinked structure. This further increases the detection sensitivity, stability in long-time measurements, and preservation stability of the enzyme sensor.

The material for enzyme layer formation may include, for example, a solution that contains an enzyme. The material for enzyme layer formation may also be a photocurable composition or a thermosetting composition. In a case of forming an enzyme layer that contains a polymeric material having a chemically bound crosslinked structure, the material for enzyme layer formation may contain at least one kind selected from a group consisting of a polymer containing a polymerizable functional group or a crosslinkable group, and a polymerizable monomer, likewise a material for absorber layer formation that will be mentioned later.

Next, the material for absorber layer formation is applied to cover the working electrode 5, the electron transport mediator layer 11, the enzyme layer 13, the reference electrode 7, and the counter electrode 9. Then, by hardening the applied material for absorber layer formation, the absorber layer 15 made from a polymeric material having a crosslinked structure is formed, and the production of the enzyme sensor 1 is thus completed. Examples of a method for hardening the material for absorber layer formation may include a use of a light source that emits radioactive rays such as ultraviolet rays. The material for absorber layer formation contains, for example, at least one kind selected from a group consisting of a polymer containing a polymerizable functional group or a crosslinkable group, and a polymerizable monomer; and a solvent. Examples of the polymer, the polymerizable monomer, and the solvent may include the following.

<1. Polymer>

The polymer containing a polymerizable functional group or a crosslinkable group is not limited to a particular polymer. Examples of such a polymer include vinyl alcohol-based polymer, acrylic polymer, vinylidene fluoride-based polymer, acrylonitrile-based polymer, and polysaccharide. Examples of the polysaccharide include cellulose derivative such as methyl cellulose, ethyl cellulose, acetyl cellulose, cellulose acetate, cellulose triacetate, alkyl cellulose, and acidic cellulose containing a carboxyl group in a side chain; hyaluronic acid; agarose; dextran; pullulan; inulin; and chitosan. Among these polymers, polyvinyl alcohol or polysaccharides are particularly preferable.

The polymer containing a polymerizable functional group is not limited to a particular polymer. Examples of such a polymer may include a polymer containing a radical polymerizable functional group and a polymer containing a cationic polymerizable functional group. The polymer containing a crosslinkable group is not limited to a particular polymer. Examples of such a polymer may include a polymer containing a group that reacts and bonds with the same group or a different group of another molecule by means of light or heat.

Examples of the radical polymerizable functional group may include a (meth)acryloyl group, a vinyl group, an allyl group, and a vinyl ether group. In respect of photo-initiated-polymerization reaction speed, the acryloyl group is preferable.

Examples of the cationic polymerizable functional group may include a propenyl ether group, a vinyl ether group, an alicyclic epoxy group, a glycidyl group, a vinyl group, and a vinylidene group. The propenyl ether group, the vinyl ether group, the alicyclic epoxy group, and the glycidyl group are preferable. Examples of the crosslinkable group may include a photo-crosslinkable group such as an azide group; and a thermally-crosslinkable group such as a hydroxyl group, a carboxyl group, an amino group, an amide group, and a mercapto group. Among these, the photo-crosslinkable group is preferable.

Examples of a polymer containing the radical polymerizable functional group may include a polymer obtained by modifying a polymer, incorporated with a functional group that reacts with an isocyanate group, with a (meth)acrylic acid derivative or a vinyl derivative containing an isocyanate group.

Examples of the polymer that reacts with an isocyanate group is preferably a polymer incorporated with a functional group that reacts with an isocyanate group. Examples of such a functional group may include a hydroxyl group, a carboxyl group, an amino group, an amide group, and a mercapto group. In other words, examples of the polymer that reacts with an isocyanate group may include a hydroxyl group-containing polymer, a carboxyl group-containing polymer, an amino group-containing polymer, an amide group-containing polymer, and a mercapto group-containing polymer.

Examples of the hydroxyl group-containing polymer may include cellulose derivative such as methyl cellulose, ethyl cellulose, acetyl cellulose, cellulose acetate, cellulose triacetate; acidic cellulose derivative containing a carboxyl group in a side chain; polyvinyl alcohol; dextran; alkyl cellulose; agarose; pullulan; inulin; chitosan; a poly-2-hydroxypropyl (meth)acrylate; and a poly-2-hydroxyethyl (meth)acrylate.

Examples of the carboxyl group-containing polymer include copolymer containing (meth)acrylic acid ester and (meth)acrylic acid as copolymer components.

Examples of the amino group-containing polymer may include polyallylamine; polyethyleneimine; poly-3-aminopropyl (meth)acrylate; poly-3-aminopropyl (meth) acrylamide; chitosan; diallylamine acetate-sulfur dioxide copolymer; and acrylamide-diallyldimethylammonium chloride copolymer.

Examples of the amide group-containing polymer may include polyvinylpyrrolidone; polyvinylcaprolactam; polyvinylpyrrolidone/vinyl acetate copolymer; vinylpyrrolidone/vinylcaprolactam copolymer; vinylpyrrolidone/vinylimidazole copolymer; vinylpyrrolidone/acrylic acid copolymer; vinylpyrrolidone/methacrylic acid copolymer; vinylpyrrolidone/3-methy-1-vinylimidazolium salt copolymer; N-vinylpyrrolidone; N-vinylpiperidone; N-vinylcaprolactam; protein; polypeptide; and oligopeptide.

Examples of the mercapto group-containing polymer may include polysulfide containing a thiol group at a chain end.

Examples of the (meth) acrylic acid derivative or the vinyl derivative containing an isocyanate group may include 2-methacryloyloxyethyl isocyanate; 2-acryloyloxyethyl isocyanate; and 2-(2-methacryloyloxyethyloxy) ethyl isocyanate. Examples of the (meth) acrylic acid derivative or the vinyl derivative containing an isocyanate group may also include derivative containing a blocked isocyanate group. For example, 1,1-(bisacryloyloxymethyl)ethyl isocyanate; methacrylic acid 2-(O-[1'-methylpropylideneamino] carboxyamino)ethyl 2-[(3,5-dimethylpyrazolyl)carbonylamino]ethyl methacrylate can be used.

Examples of a polymer containing the cationic polymerizable functional group may include a polymer having a structural unit derived from an epoxy group-containing vinyl monomer that contains a polymerizable vinyl group (group having ethylenically unsaturated bond) and one or more epoxy groups in one molecule.

Examples of the epoxy group-containing vinyl monomer include non-hydroxyl group-containing (meth)acrylic acid esters such as glycidyl (meth) acrylate, 4-hydroxybutyl (meth)acrylate glycidyl ether, 3,4-epoxycyclohexylmethyl (meth)acrylate, and α-(meth)acryl-ω-glycidyl polyethylene glycol; hydroxyl group-containing (meth)acrylic acid esters such as glycerin mono(meth)acrylate glycidyl ether; aromatic monovinyl compounds such as vinylbenzyl glycidyl ether; allyl glycidyl ether; 3,4-epoxy-1-butene; and 3,4-epoxy-3-methyl-1-butene. Among these, one monomer may be used alone, or two or more monomers may be used in combination.

Among the above monomers, an epoxy group-containing monovinyl monomer is preferably an epoxy group-containing (meth)acrylic acid ester or an epoxy group-containing aromatic monovinyl compound, more preferably epoxy group-containing (meth) acrylic acid esters, yet more preferably a glycidyl (meth)acrylate or 4-hydroxybutyl (meth) acrylate glycidyl ether, and particularly preferably a glycidyl (meth)acrylate.

The polymer containing a structural unit derived from the epoxy group-containing vinyl monomer may be a copolymer containing a structural unit derived from a monomer other than the epoxy group-containing vinyl monomer. Examples of the monomer other than the epoxy group-containing vinyl monomer include (meth)acrylic acid esters such as methyl (meth) acrylate, ethyl (meth)acrylate, butyl (meth)acrylate, cyclohexyl (meth)acrylate, and methoxyethyl (meth) acrylate; and (meth)acrylamides such as (meth)acrylamide, dimethyl (meth)acrylamide, (meth)acryloylmorpholine, and diacetone (meth)acrylamide. One kind of these monomers may be used alone or two or more kinds of these monomers may be used in combination.

As a polymer containing a crosslinkable group, the polymers raised in the aforementioned examples such as hydroxyl group-containing polymer, carboxyl group-containing polymer, amino group-containing polymer, amide group-containing polymer, and mercapto group-containing polymer may be used. Examples of a polymer containing a photo-crosslinkable group, such as an azide group, may include polymers such as polyvinyl alcohol and polysaccharide that contain aryl azide group, diazirine group, 5-azide-2-nitrophenyl group, and the like in the side chain.

With the object of obtaining the absorber layer particularly excellent in durability, the lower limit of the amount of the crosslinkable groups in the polymer is preferably 0.01 mmol/g or greater, more preferably 0.05 mmol/g or greater, yet more preferably 0.1 mmol/g or greater, still more preferably 0.5 mmol/g or greater, and particularly preferably 1.0 mmol/g or greater. With the object of obtaining the absorber layer particularly excellent in absorptivity with respect to the secretion of the living body, the upper limit of the amount of the crosslinkable group in the polymer is preferably 50 mmol/g or less, more preferably 20 mmol/g or less, yet more preferably 10 mmol/g or less, still more preferably 5 mmol/g or less, and particularly preferably 2.0 mmol/g or less.

The weight-average molecular weight (Mw) of the polymer in polystyrene conversion measured by gel permeation chromatography (GPC) is preferably 5,000 or greater and 200,000 or less, and more preferably 10,000 or greater and 100,000 or less. If the weight-average molecular weight of the polymer is below the range mentioned above, the strength of the resulting absorber layer may not be sufficient. If the weight-average molecular weight is above the range mentioned above, it may pose difficulties in forming the absorber layer due to increased viscosity.

With the object of obtaining the absorber layer particularly excellent in durability, the amount of the polymer in the composition for absorber layer formation described above is preferably 0.1 percent by mass or greater, more preferably 0.5 percent by mass or greater, and yet more preferably 1 percent by mass or greater. With the object of obtaining the absorber layer particularly excellent in water absorptivity, the amount of the polymer in the composition for absorber layer formation described above is preferably 30 percent by mass or less, more preferably 20 percent by mass or less, and yet more preferably 10 percent by mass or less.

<2. Polymerizable Monomer>

The polymerizable monomer will be explained next. The polymerizable monomer is not limited to a particular monomer. Examples of such a monomer include radical polymerizable unsaturated compound and cationic polymerizable compound.

<2-1. Radical Polymerizable Unsaturated Compound>

The radical polymerizable unsaturated compound means a polymerizable unsaturated compound capable of initiating polymerization by a radical species, for example, carboxyl group-containing unsaturated compound; hydroxyl group-containing radical polymerizable unsaturated compound; reactant of hydroxyl group-containing radical polymerizable unsaturated compound and lactone compound; (meth) acrylic acid esters; aromatic vinyl compound; (meth)acrylamides; and alkoxysilyl group-containing radical polymerizable unsaturated compound.

Examples of the carboxyl group-containing unsaturated compound may include acrylic acid; methacrylic acid; and maleic acid. Examples of the hydroxyl group-containing radical polymerizable unsaturated compound may include C2-C8 hydroxyalkylesters of acrylic acid or methacrylic acid such as 2-hydroxyethyl (meth)acrylate; (poly)ethylene glycol mono(meth)acrylate; and polypropylene glycol mono (meth)acrylate. Examples of the (meth) acrylic acid esters may include methyl (meth)acrylate, and ethyl (meth)acrylate. Examples of the aromatic vinyl compound may include styrene; α-methylstyrene; vinyltoluene; p-chlorostyrene; and vinylpyridine. Examples of the (meth)acrylamides may include N,N-dimethylacrylamide; and N-(2-hydroxyethyl) (meth)acrylamide. Examples of the alkoxysilyl group-containing radical polymerizable unsaturated compound include vinyltrimethoxysilane; vinylmethyldimethoxysilane; vinyldimethylmethoxysilane; and γ-(meth)acryloyloxypropyldimethylmethoxysilane.

The aforementioned examples are of compounds having one radical polymerizable unsaturated bond in one molecule, but are not a particular limitation. Compounds having two or more radical polymerizable unsaturated bonds in one molecule may also be used; specific examples include divinylbenzene, and ethylene glycol di(meth)acrylate.

<2-2. Cationic Polymerizable Compound>

The cationic polymerizable compound means a polymerizable compound capable of initiating polymerization by a cationic species, for example, epoxy compound; oxetane compound; and vinyl compound. One of these compounds may be used alone, or two or more of these compounds may be used in combination.

As the epoxy compound, aliphatic epoxy and alicyclic epoxy can all be used. With respect to the aliphatic epoxy, an appropriate aliphatic epoxy can be selected in accordance with the purpose without particular limitations. Examples of the epoxy compound may include aliphatic polyhydric alcohol or polyglycidyl ethers, which is an alkylene oxide adduct of the aliphatic polyhydric alcohol. Specific examples of the epoxy compound may include ethylene glycol diglycidyl ether, and trimethylolpropane triglycidyl ether. Examples of the alicyclic epoxy compound may include vinylcyclohexene monoxide, and 1,2-epoxy-4-vinylcyclohexane. One of the aforementioned compounds may be used alone, or two or more of these compounds may be used in combination.

An oxetane compound contains a four-membered cyclic ether, that is, an oxetane ring in a molecule. An appropriate oxetane compound can be selected in accordance with the purpose without particular limitations; examples may include 3-ethyl-3-hydroxymethyloxetane; and 1,4-bis[{(3-ethyl-3-oxetanyl)methoxy}methyl]benzene. One of these compounds may be used alone, or two or more of these compounds may be used in combination.

An appropriate vinyl compound may be selected in accordance with the purpose without particular limitations as long as the compound is capable of cationic polymerization; examples may include styrene compound, and vinyl ether compound.

With the object of obtaining the absorber layer particularly excellent in durability, the amount of the polymerizable monomer in the composition for absorber layer formation described above is preferably 1 percent by mass or greater, more preferably 5 percent by mass or greater, yet more preferably 10 percent by mass or greater, and particularly preferably 20 percent by mass or greater. With the object of obtaining the absorber layer particularly excellent in water absorptivity, the amount of the polymerizable monomer in the composition for absorber layer formation described above is preferably 95 percent by mass or less, more preferably 90 percent by mass or less, yet more preferably 80 percent by mass or less, and particularly preferably 70 percent by mass or less.

With the object of obtaining the absorber layer particularly excellent in durability, the amount of the polymerizable monomer with respect to 100 parts by mass of the polymer is preferably 10 parts by mass or greater, more preferably 20 parts by mass or greater, yet more preferably 50 parts by mass or greater, and particularly preferably 100 parts by mass or greater. With the object of obtaining the absorber layer particularly excellent in water absorptivity, the amount of the polymerizable monomer with respect to 100 parts by mass of the polymer is preferably 10,000 parts by mass or less, more preferably 5,000 parts by mass or less, yet more preferably 3,000 parts by mass or less, and particularly preferably 2,000 parts by mass or less.

<3. Solvent>

The composition for absorber layer formation used in the present disclosure may include a solvent. Preferably, the composition for absorber layer formation includes a solvent with the object of obtaining the absorber layer particularly excellent in flexibility and mechanical strength. Although examples of the solvent include alcohol and water, water is particularly preferable.

With the object of obtaining the absorber layer excellent in absorptivity with respect to the secretion of the living body, the amount of the solvent with respect to 100 percent by mass of the composition for absorber layer formation is preferably 1 percent by mass or greater, more preferably 5 percent by mass or greater, yet more preferably 10 percent by mass or greater, and particularly preferably 20 percent by mass or greater. With the object of obtaining the absorber layer particularly excellent in durability, the amount of the solvent with respect to 100 percent by mass of the composition for absorber layer formation is preferably 99 percent by mass or less, more preferably 95 percent by mass or less, yet more preferably 90 percent by mass or less, and particularly preferably 80 percent by mass or less.

With the object of obtaining a water absorber layer excellent in water absorptivity, the amount of the solvent with respect to 100 parts by mass of the total mass of the polymer and polymerizable monomer is preferably 1 parts by mass or greater, more preferably 5 parts by mass or greater, yet more preferably 10 parts by mass or greater, and particularly preferably 20 parts by mass or greater. With the object of obtaining the absorber layer particularly excellent in durability, the amount of the solvent with respect to 100 parts by mass of the total mass of the polymer and polymerizable monomer is preferably 10,000 parts by mass or less, more preferably 5,000 parts by mass or less, yet more preferably 1,000 parts by mass or less, and particularly preferably 400 parts by mass or less.

<4. Photo Radical Generator, Photo Acid Generator, and Crosslinking Accelerator>

With the object of obtaining the absorber layer excellent in durability, it is desirable that the composition for absorber layer formation used in the present disclosure comprises at least one or more selected from a group consisting of a photo radical generator, a photo acid generator, and a crosslinking accelerator in a case where the composition comprises a polymerizable monomer such as radical polymerizable unsaturated compound and cationic polymerizable compound.

<5. Crosslinking Agent>

With the object of obtaining the absorber layer excellent in durability, it is desirable that the composition for absorber layer formation used in the present disclosure comprises a crosslinking agent in a case where the composition comprises a polymer containing a crosslinkable group.

<6. Other Components>

With the object of obtaining a function in accordance with the intended use, the composition for absorber layer formation used in the present disclosure may comprise additives such as colorant, filler, plasticizer, stabilizer, colorant, aging inhibitor, antioxidant, antistatic agent, weather resistant agent, ultraviolet ray absorber, anti-blocking agent, crystal nucleating agent, flame retardant, vulcanizing agent, vulcanization aid, antibacterial/antifungal agent, dispersant, coloration inhibitor, foaming agent, and anti-rust agent to the extent that the effect of the present disclosure is not compromised.

3. Operation of Enzyme Sensor 1

The absorber layer 15 contacts the living body when the enzyme sensor 1 is in use. The absorber layer 15 absorbs the secretion of the living body. The secretion of the living body absorbed by the absorber layer 15 passes through the absorber layer 15 and reaches the enzyme layer 13. The enzyme layer 13 produces an electrode-detectable substance or a precursor of electrode-detectable substance from the measurement target substance contained in the secretion of the living body in the presence of an enzyme.

Next, an electrode-detectable substance is generally produced from the precursor of electrode-detectable substance in the electron transport mediator layer 11 by an oxidation-reduction reaction of the electron transport mediator. The electrode-detectable substance produced in the electron transport mediator layer 11 then causes an electrochemical reaction including the oxidation-reduction reaction on a surface of the working electrode 5. This causes an electric current to occur in the enzyme sensor 1, which then causes the enzyme sensor 1 to electrically detect the concentration of the electrode-detectable substance. Accordingly, an electric current in accordance with the concentration of the measurement target substance contained in the secretion of the living body occurs in the enzyme sensor 1; and the concentration of the measurement target substance is electrically detected by the enzyme sensor 1.

For example, in a case of measuring lactic acid contained in perspiration, the enzyme layer 13 oxidizes lactic acid contained in perspiration in the presence of lactate oxidase to generate pyruvic acid and hydrogen peroxide. In the electron transport mediator layer 11, the electron transport mediator such as ferrocene produces a complex of ferrocene and pyruvic acid that corresponds to the electrode-detectable substance in conjugation with the oxidation-reduction reaction in the enzyme layer 13. The complex of ferrocene and pyruvic acid produced in the electron transport mediator layer 11 then causes the electrochemical reaction including the oxidation-reduction reaction on the surface of the working electrode 5, and the concentration of the electrode-detectable substance is electrically detected. Accordingly, an electric current in accordance with the concentration of lactic acid occurs in the enzyme sensor 1, which causes the enzyme sensor 1 to electrically detect the concentration of lactic acid.

If there is no electron transport mediator layer 11, the electrode-detectable substance produced in the enzyme layer 13 directly causes the electrochemical reaction, including the oxidation-reduction reaction, on the surface of the working electrode 5, which causes an electric current to occur in the enzyme sensor 1 and then causes the enzyme sensor 1 to electrically detect the concentration of the electrode-detectable substance.

4. Effect of Enzyme Sensor 1

(1A) The enzyme sensor 1 is excellent in detection sensitivity, repeat reactivity, and preservation stability. The enzyme sensor 1 is not prone to have its detection sensitivity decreased when a measurement is carried out for a long time.

(1B) The absorber layer 15 is positioned to be in contact with the living body when the enzyme sensor 1 is in use. This facilitates absorption of the secretion of the living body by the absorber layer 15.

(1C) The enzyme layer 13 produces the electrode-detectable substance or the precursor of electrode-detectable substance from the measurement target substance contained in the secretion of the living body in the presence of enzyme. An electric current that reflects the concentration of the measurement target substance contained in a secretion of a living body occurs in the enzyme sensor 1. This further improves the detection sensitivity of the enzyme sensor 1 with respect to lactic acid.

(1D) The enzyme sensor 1 electrically detects the concentration of the electrode-detectable substance. Since the electrode-detectable substance is produced from the measurement target substance contained in the secretion of the living body, there is a correlative relationship between the concentration of the electrode-detectable substance and the concentration of the measurement target substance contained in the secretion of the living body. Thus, the enzyme sensor 1 is capable of electrically detecting the concentration of the measurement target substance contained in the secretion of the living body.

(1E) The enzyme sensor 1 comprises the electron transport mediator layer 11 between the working electrode 5 and the enzyme layer 13. This further improves the detection sensitivity of the enzyme sensor 1.

(1F) The enzyme sensor 1 further comprises the base material layer 3 that supports the working electrode 5, the reference electrode 7, and the counter electrode 9. The structure of the enzyme sensor 1 is therefore stabilized.

(1G) With reference to JIS7209, the water absorption ratio of the absorber layer 15 is 10% or greater and 100,000% or less. This further increases the amount of the secretion of the living body absorbed by the absorber layer 15. As a result of this, the detection sensitivity of the measurement target substance contained in the secretion of the living body is further improved.

(1H) The absorber layer 15 can be made from the photocurable composition. The absorber layer 15 is irradiated with light as it is made from the photocurable composition. This facilitates production of a polymeric material having a chemically bound crosslinked structure in the absorber layer 15.

SECOND EMBODIMENT

1. Difference from First Embodiment

Since the basic configuration in the second embodiment is the same as that of the first embodiment, their differences will be explained hereinafter. The same reference numeral as the first embodiment indicates an identical configuration; and for the identical configuration, reference should be made to the antecedent explanation.

Figure 3:
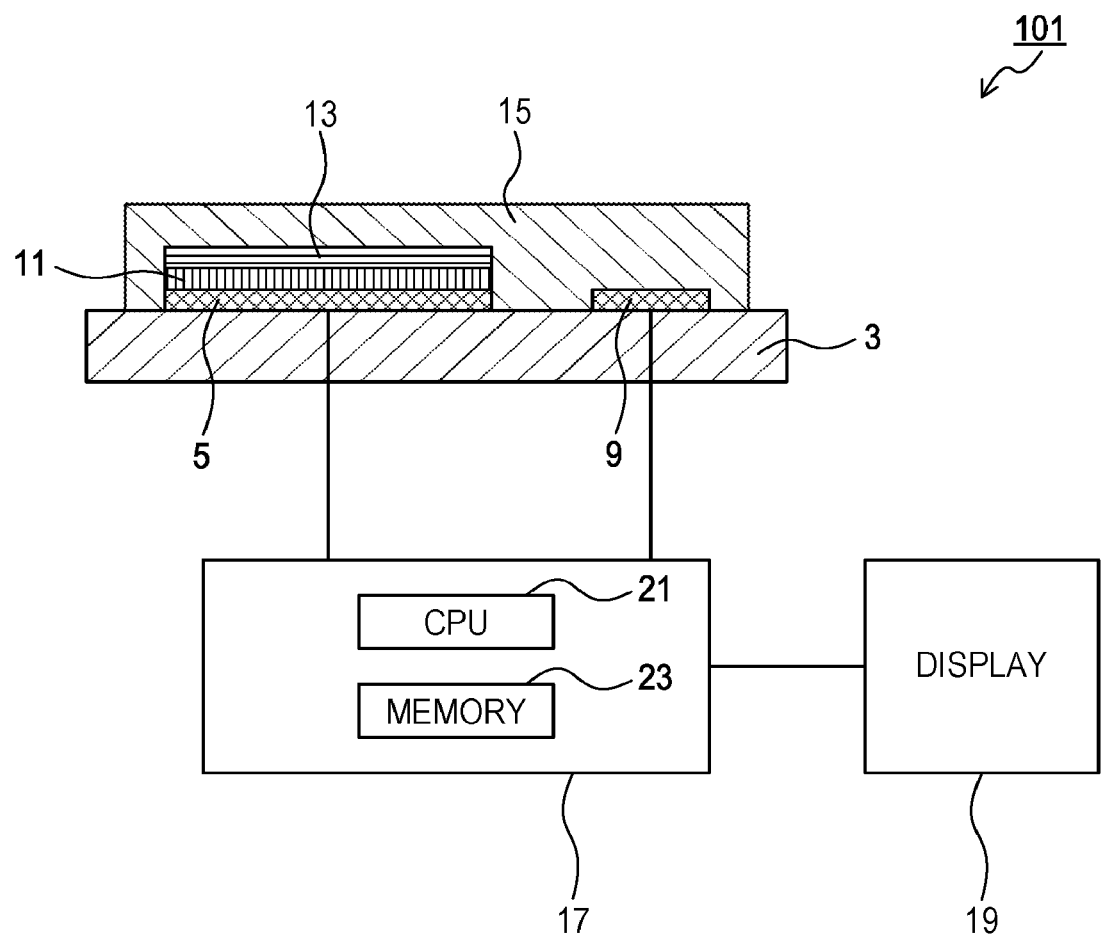
FIG. 3 is an explanatory diagram showing the configuration of the enzyme sensor.

As shown in FIG. 3, an enzyme sensor 101 comprises an arithmetic unit 17 and a display 19 in addition to the configuration in the aforementioned first embodiment. The arithmetic unit 17 is electrically coupled to the working electrode 5, the reference electrode 7, and the counter electrode 9. The arithmetic unit 17 is configured mainly with a well-known microcomputer that comprises a CPU 21, and a semiconductor memory (hereinafter referred to as the memory 23) such as a RAM, a ROM, and a flash memory. Functions of the arithmetic unit 17 are performed by the CPU 21 executing a program stored in a non-transitory tangible storage medium. In this embodiment, the memory 23 corresponds to the non-transitory tangible storage medium comprising the program. The execution of the program in turn executes a method that corresponds to the program. The number of the microcomputer that configures the arithmetic unit 17 may be one, or two or more. All or a part of the functions of the arithmetic unit 17 may be performed like a hardware, by using one or more ICs or the like.

The arithmetic unit 17 is configured with a correspondence table between the detected results detected in the working electrode 5, the reference electrode 7, and the counter electrode 9, and the concentration of the measurement target substance contained in the secretion of the living body. The arithmetic unit 17 uses the table and calculates the concentration of the measurement target substance contained in the secretion of the living body based on the detected results obtained in the working electrode 5, the reference electrode 7, and the counter electrode 9. The display 19 shows the result of the calculation by the arithmetic unit 17.

2. Effect of Enzyme Sensor 101

The second embodiment, which has been explained in detail above, exerts the following effect in addition to the aforementioned effects of the first embodiment.

(2A) The enzyme sensor 101 can calculate the concentration of lactic acid with the arithmetic unit 17.

THIRD EMBODIMENT

1. Configuration of Enzyme Sensor System 200

Figure 4:
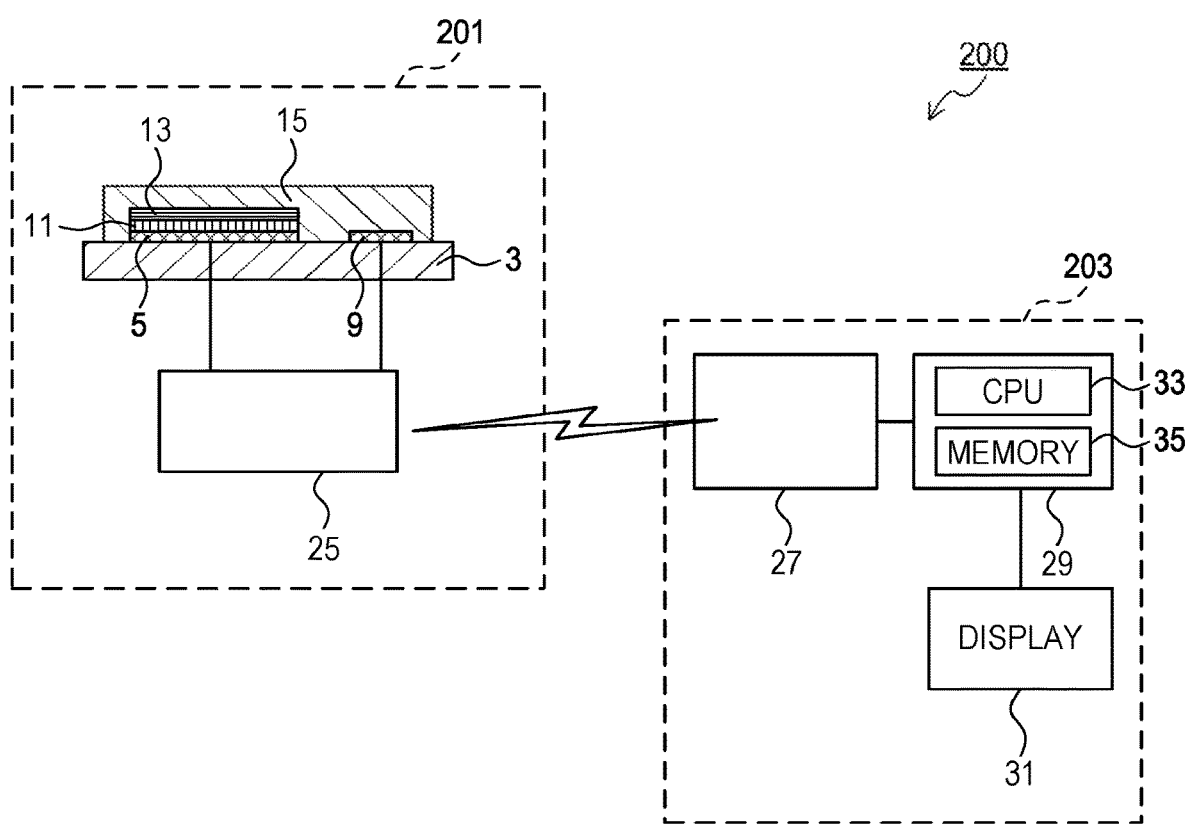
FIG. 4 is an explanatory diagram showing a configuration of an enzyme sensor system.

As shown in FIG. 4, an enzyme sensor system 200 comprises an enzyme sensor 201, and an arithmetic device 203. Since the basic configuration of the enzyme sensor 201 is the same as the enzyme sensor 1 in the first embodiment, their differences will be explained hereinafter. The reference numeral same as that of the first embodiment indicates an identical configuration; and for the identical configuration, reference should be made to the antecedent explanation. The enzyme sensor 201 further comprises a data transmission unit 25 in addition to the configuration of the enzyme sensor 1 in the first embodiment.

The data transmission unit 25 is electrically coupled to the working electrode 5, the reference electrode 7, and the counter electrode 9. The data transmission unit 25 transmits data that shows detected results (hereinafter referred to as the detected data) in the working electrode 5, the reference electrode 7, and the counter electrode 9 via wireless communication or wired communication.

The arithmetic device 203 comprises a data receiving unit 27, a receiver-side arithmetic unit 29, and a display 31. The data receiving unit 27 receives the detected data transmitted by the data transmission unit 25 and transmits the received detected data to the receiver-side arithmetic unit 29.

The receiver-side arithmetic unit 29 is configured mainly with a well-known microcomputer that comprises a CPU 33, and a semiconductor memory (hereinafter referred to as the memory 35) such as a RAM, a ROM, and a flash memory. Functions of the receiver-side arithmetic unit 29 are performed by the CPU 33 executing a program stored in a non-transitory tangible storage medium. In this embodiment, the memory 35 corresponds to the non-transitory tangible storage medium comprising the program. The execution of the program in turn executes a method that corresponds to the program. The number of the microcomputer that configures the receiver-side arithmetic unit 29 may be one, or two or more. All or a part of the functions of the receiver-side arithmetic unit 29 may be performed like a hardware, by using one or more ICs or the like.

The receiver-side arithmetic unit 29 is configured with a correspondence table between the detected results included in the detected data and the concentration of lactic acid contained in perspiration. The receiver-side arithmetic unit 29 uses the table and calculates the concentration of lactic acid contained in perspiration based on the detected data. The display 31 shows the result of calculation by the receiver-side arithmetic unit 29.

2. Effect of Enzyme Sensor System 200

The third embodiment, which has been explained in detail above, exerts the following effect in addition to the aforementioned effects of the first embodiment.

(3A) The enzyme sensor 201 can transmit the detected data. The arithmetic device 203 can receive the transmitted detected data and calculate the concentration of lactic acid contained in perspiration based on the detected data. The enzyme sensor 201 need not comprise a configuration to calculate the concentration of lactic acid contained in perspiration; thus, the volume and weight of the enzyme sensor 201 can be reduced.

OTHER EMBODIMENTS

Although the embodiments of the present disclosure have been explained above, the present disclosure may be carried out in various forms without being limited to the aforementioned embodiments.

(1) The secretion of the living body absorbed in the absorber layer 15 may be a substance other than perspiration, for example, saliva, tears, urine, and blood.

(2) The measurement target substance may be a substance other than lactic acid, for example, substances such as glucose.

(3) The enzyme contained in the enzyme layer 13 may be other enzyme, for example, enzymes such as glucose oxidizing enzyme. In a case where the enzyme layer 13 contains glucose oxidizing enzyme, the enzyme sensor may measure glucose contained in the secretion of the living body.

Figure 5:
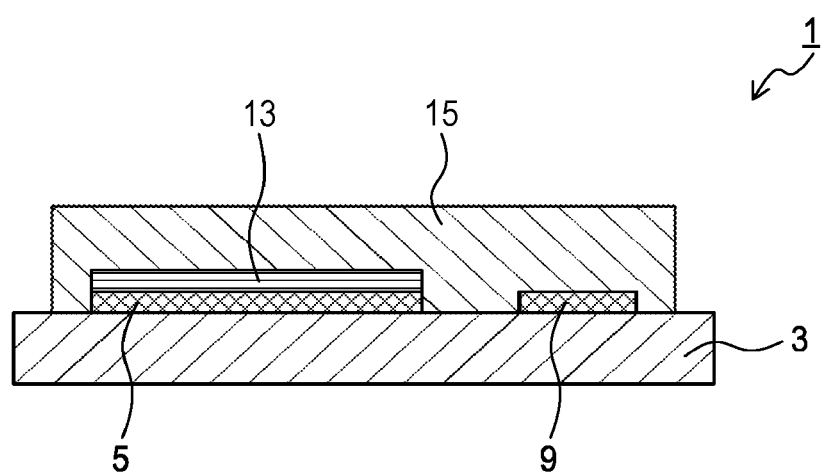
FIG. 5 is an explanatory diagram showing a configuration of an enzyme sensor in a different embodiment.

(4) As shown in FIG. 5, the enzyme sensor 1 need not comprise an electron transport mediator layer. In this case, the working electrode 5 and the enzyme layer 13 are situated adjacent to each other.

(5) The absorber layer 15 may include a thermosetting composition. In this case, the absorber layer 15 that includes a polymeric material having a chemically bound crosslinked structure can be formed by heating.

(6) The enzyme layer 13 may include a polymeric material having a chemically bound crosslinked structure. In this case, the detection sensitivity, repeat reactivity, and preservation stability of the enzyme sensor are further improved.

(7) The arithmetic unit 17 in the second embodiment may calculate the amount of lactic acid instead of or in addition to the concentration of lactic acid. For example, the arithmetic unit 17 may measure the amount of perspiration and then calculate the amount of lactic acid by multiplying the amount of perspiration by the concentration of lactic acid.

(8) The arithmetic device 203 in the third embodiment may calculate the amount of lactic acid instead of or in addition to the concentration of lactic acid. For example, the arithmetic device 203 may calculate the amount of lactic acid by multiplying the amount of perspiration by the concentration of lactic acid. The enzyme sensor 201 may measure the amount of perspiration and transmit the measured amount of perspiration to the arithmetic device 203.

(9) The absorber layer 15 need not cover one of the reference electrode 7 or the counter electrode 9, or both of the reference electrode 7 and the counter electrode 9.

(10) Functions of one element in the aforementioned embodiments may be performed by two or more elements, or functions of two or more elements may be performed by one element. A part of the configuration in the aforementioned embodiments may be omitted. At least a part of the configurations in the aforementioned embodiments may be added to or replaced with other configuration of the aforementioned embodiments. It should be noted that any and all modes that are encompassed in the technical ideas that are defined by the languages in the claims are embodiments of the present disclosure.

(11) In addition to the enzyme sensor and the enzyme sensor system mentioned above, the present disclosure may be carried out in various forms, which may be a program to make a computer function as the arithmetic unit 17 or as the receiver-side arithmetic unit 29, a non-transitory tangible storage medium such as a semiconductor memory storing this program, measuring methods of the measurement target substance included in the secretion of the living body, and so on.

EXAMPLES

1. Production of Enzyme Sensor
(1) Enzyme Sensor 1
The working electrode 5 and the counter electrode 9 as shown in FIG. 1 were formed by applying an ink containing carbon (carbon-graphite ink: C2030519P4, Gwent Electronic Materials, UK) by screen printing on the base material layer 3 with a size of 40 mm×10 mm. And, the reference electrode 7 as shown in FIG. 1 was formed by applying an ink containing silver and silver chloride (C2130809D5, Gwent Electronic Materials, UK) by screen printing on the base material layer 3.

Next, the electron transport mediator layer 11 was formed by applying 0.5 µL of acetone solution containing ferrocene with the concentration of 50 mmol/L on a circular part of the working electrode 5, and drying the applied solution at room temperature.

Next, the enzyme layer 13 was formed by applying 1.0 µL of PBS solution (0.1 mol/L of phosphate buffer solution with PH7.0) containing lactate oxidase with the concentration of 0.5 percent by weight on the electron transport mediator layer 11, and drying the applied solution at room temperature.

Next, BIOSURFINE (registered trademark)-AWP (manufactured by Toyo Gosei Co., Ltd.) was applied over the working electrode 5, the electron transport mediator layer 11, the enzyme layer 13, the reference electrode 7, and the counter electrode 9 with a film applicator to obtain a film thickness of 10 µm when the film was dried. Then, the film was irradiated with ultraviolet rays with the wavelength of 365 nm and the intensity of 2.0 mW/cm$^2$ for five minutes by using a light source (MAX-301, manufactured by Asahi Spectra Co., Ltd.) to form the absorber layer 15 made from a polymeric material having a chemically bound crosslinked structure. The enzyme sensor 1 was thus completed. The BIOSURFINE-AWP is a photo-crosslinking water soluble resin composition, which corresponds to a photocurable composition.

(2) Enzyme Sensor 2
The working electrode 5 and the counter electrode 9 as shown in FIG. 1 were formed by applying an ink containing carbon (carbon-graphite ink: C2030519P4, Gwent Electronic Materials, UK) by screen printing on the base material layer 3 with a size of 40 mm×10 mm. And, the reference electrode 7 as shown in FIG. 1 was formed by applying an ink containing silver and silver chloride (C2130809D5, Gwent Electronic Materials, UK) by screen printing on the base material layer 3.

Next, the electron transport mediator layer 11 was formed by applying 0.5 µL of acetone solution containing ferrocene with the concentration of 50 mmol/L on the circular part of the working electrode 5, and drying the applied solution at room temperature.

Next, the enzyme layer 13 was formed by applying 1.0 µL of PBS solution (0.1 mol/L of phosphate buffer solution with PH7.0) containing lactate oxidase with the concentration of 0.5 percent by weight on the electron transport mediator layer 11, and drying the applied solution at room temperature.

Next, 0.102 g of cellulose derivative (hydroxypropyl cellulose, HPC) was added to 7.93 g of N,N-dimethylacrylamide, and this mixture was stirred until the HPC dissolved. Then, 0.3 molar amount of KarenzMOI-EG (registered trademark, manufactured by Showa Denko K.K.) per one mole of pyranose ring, which was a constituent unit (monomer) of the HPC, was added to the mixture, and the mixture was stirred for one hour at 60° C. Then, 20 mL of pure water was added to cause unreacted isocyanate groups in the KarenzMOI-EG to react with water molecules, which yielded reaction product of cellulose derivative and KarenzMOI-EG as a polymer. The amount of the crosslinkable groups in the yielded polymer was 0.09 mmol/g. Then, 0.012 g of α-ketoglutaric acid, which was a photo radical initiator, was added to prepare a photo-crosslinking water soluble resin composition (A1).

Next, the photo-crosslinking water soluble resin composition (A1) was applied over the working electrode 5, the electron transport mediator layer 11, the enzyme layer 13, the reference electrode 7, and the counter electrode 9 with a film applicator to obtain the film thickness of 10 μm when the film was dried. Then, the film was irradiated with ultraviolet rays with the wavelength of 365 nm and the intensity of 2.0 mW/cm$^2$ for 10 minutes by using the light source (MAX-301, manufactured by Asahi Spectra Co., Ltd.) to form the absorber layer 15 made from a polymeric material having a chemically bound crosslinked structure. The enzyme sensor 2 was thus completed. The photo-crosslinking water soluble resin composition (A1) contains a photo-crosslinking water soluble resin and corresponds to photo curable composition.

(3) Enzyme Sensor 3

The basic configuration of an enzyme sensor 3 is the same as that of the enzyme sensor 1. Nevertheless, the photo-crosslinking water soluble resin composition (A1) for forming the absorber layer 15 was produced as follows.

First, next, 0.102 g of cellulose derivative (hydroxypropyl cellulose, HPC) was added to 7.93 g of N,N-dimethylacrylamide, and this mixture was stirred until the HPC dissolved. Then, 1.5 molar amount of the KarenzMOI-EG per one mole of pyranose ring, which was a constituent unit (monomer) of the HPC, was added to the mixture, and the mixture was stirred for one hour at 60° C. Then, 20 mL of pure water was added to cause unreacted isocyanate groups in the KarenzMOI-EG to react with water molecules, which yielded reaction product of cellulose derivative and KarenzMOI-EG as a polymer. The amount of the crosslinkable groups in the yielded polymer was 0.43 mmol/g. Then, 0.012 g of α-ketoglutaric acid, which was a photo radical initiator, was added to prepare the photo-crosslinking water soluble resin composition (A1).

(3) Enzyme Sensor 4

The basic configuration of an enzyme sensor 4 is the same as that of the enzyme sensor 1. Nevertheless, the photo-crosslinking water soluble resin composition (A1) for forming the absorber layer 15 was produced as follows.

First, 0.204 g of cellulose derivative (hydroxypropyl cellulose, HPC) was added to 7.93 g of N,N-dimethylacrylamide, and this mixture was stirred until the HPC dissolved. Then, 2.1 molar amount of the KarenzMOI-EG per one mole of pyranose ring, which was a constituent unit (monomer) of the HPC, was added to the mixture, and the mixture was stirred for one hour at 60° C. Then, 20 mL of pure water was added to cause unreacted isocyanate groups in the KarenzMOI-EG to react with water molecules, which yielded reaction product of cellulose derivative and KarenzMOI-EG as a polymer. The amount of the crosslinkable groups in the yielded polymer was 1.22 mmol/g. Then, 0.012 g of α-ketoglutaric acid, which was a photo radical initiator, was added to prepare the photo-crosslinking water soluble resin composition (A1).

(5) Enzyme Sensor 5

The basic configuration of an enzyme sensor 5 is the same as that of the enzyme sensor 1. Nevertheless, the enzyme layer 13 was formed as follows. First, the PBS solution (0.1 mol/L of phosphate buffer solution with PH7.0) containing lactase oxidase with the concentration of 1.5 percent by weight and the BIOSURFINE (registered trademark)-AWP (manufactured by Toyo Gosei Co., Ltd.) were mixed at the mass ratio of 1:1 to prepare a mixed solution. Then, 1.0 μl of the mixed solution was applied on the electron transport mediator layer 11 and dried at room temperature to form the enzyme layer 13.

(6) Enzyme Sensors R1, R2, and R3

Although the basic configuration is the same as that of the enzyme sensor 1, an enzyme sensor R1 was produced without irradiation of ultraviolet rays when forming the absorber layer 15. The absorber layer 15 of the enzyme sensor R1 does not have a chemically bound crosslinked structure.

Although the basic configuration is the same as that of the enzyme sensor 1, an enzyme sensor R2 was produced without the absorber layer 15.

Although the basic configuration is the same as that of the enzyme sensor 1, an enzyme sensor R3 was produced without the enzyme layer 13.

2. Evaluation of Absorber Layers of Enzyme Sensors

The absorber layers 15 used in the enzyme sensors 1 and 2 were formed as follows. A photocurable composition was applied on the base material layer 3 with the film applicator to obtain the film thickness of 10 μm and the size of 50 mm×50 mm when the film was dried. The photocurable composition for the absorber layer 15 used in the enzyme sensor 1 was the BIOSURFINE-AWP; the photocurable composition for the absorber layer 15 used in the enzyme sensor 2 was the photo-crosslinking water soluble resin composition (A1).

Next, the applied film was irradiated with ultraviolet rays with the wavelength of 365 nm and the intensity of 2.0 mW/cm$^2$ for ten minutes by using the light source (MAX-301, manufactured by Asahi Spectra Co., Ltd.). As a result, the absorber layer 15 made from a polymeric material having a chemically bound crosslinked structure was obtained.

The absorption ratio of the obtained absorber layer 15 was calculated from a mass change of the absorber layer 15 before and after being immersed in water at 23° C. for 24 hours. The method of calculating the absorption ratio was conforming to JIS7209. The water absorption ratio of the absorber layer 15 used in the enzyme sensor 1 and the absorber layer 15 used in the enzyme sensor 2 were respectively 900%, and 9900%. The water absorption ratio of the absorber layer 15 used in the enzyme sensor 3 and the absorber layer 15 used in the enzyme sensor 4 were respectively 2500%, and 800%.

3. Evaluation of Enzyme Sensors

The enzyme sensors 1, 2, 3, 4, and 5, and the enzyme sensors R1, R2, and R3 were evaluated as follows.

(3-1) Preparation of Measurement Solution

A measurement solution A, and a measurement solution B for evaluation were prepared as below. The measurement solution A and the measurement solution B were stimulant liquids simulating secretions of a living body. L-lactic acid contained in the measurement solution B corresponds to the measurement target substance contained in the secretions.

Measurement solution A: 0.1 mol/L of phosphate buffer solution with PH7.0

Measurement solution B: 50 mmol/L of L-lactic acid PBS solution (0.1 mol/L of phosphate buffer solution with PH7.0)

(3-2) Evaluation of Detection Sensitivity

The enzyme sensors were attached to a compact potentiostat (miniSTAT100, manufactured by BioDevice Technology, Ltd.) and immersed in the measurement solution A. A potential of 0.2 V was applied to the enzyme sensors. The enzyme sensors were left still until current values in the enzyme sensors were constant. Then, the enzyme sensors were immersed in the measurement solution B, and the amount of changes in the current values were measured. If the amount of change in the current value was 2 μA or greater, then the enzyme sensor was evaluated to have an excellent detection sensitivity. If the amount of change is 1 µA or greater and less than 2 µA, then the enzyme sensor was evaluated to have a good detection sensitivity. If the amount of change is less than 1 µA, then the enzyme sensor was evaluated to have an insufficient detection sensitivity. Table 1 shows the result of the evaluation. In Table 1, in the column of "Detection Sensitivity", the mark "⊚" means that the detection sensitivity of the enzyme sensor was excellent; the mark "○" means that the detection sensitivity of the enzyme sensor was good; and the mark "X" means that the detection sensitivity of the enzyme sensor was insufficient.

immersed in the measurement solution B, and the amount of change in the current value were measured.

A value (hereinafter referred to as after/before storage ratio) was calculated by dividing the amount of change in current value after storage by the amount of change in current value before storage, and multiplying the result by 100. If the after/before storage ratio was 90% or greater, then the preservation stability of the enzyme sensor was evaluated as excellent. If the after/before storage ratio was 80% or greater and less than 90%, then the preservation stability of the enzyme sensor was evaluated as good. If the after/

TABLE 1

| Evaluation Method | Enzyme Sensor 1 | Enzyme Sensor 2 | Enzyme Sensor 3 | Enzyme Sensor 4 | Enzyme Sensor 5 | Enzyme Sensor R1 | Enzyme Sensor R2 | Enzyme Sensor R3 |
|---|---|---|---|---|---|---|---|---|
| Detection Sensitivity | ⊚ | ⊚ | ⊚ | ⊚ | ⊚ | ○ | X | X |
| Repeat Reactivity | ⊚ | ○ | ○ | ⊚ | ⊚ | X | X | X |
| Preservation Stability | ○ | ○ | ○ | ○ | ⊚ | ○ | X | X |
| Crosslinking Concentration | 2 mmol % | 0.09 mmol | 0.4 mmol | 1.2 mmol | | | | |
| Water Absorption Ratio | 900 | 9900 | 2500 | 800 | | | | |

(3-3) Evaluation of Repeat Reactivity (i) The enzyme sensors were attached to the compact potentiostat (miniSTAT100, manufactured by BioDevice Technology, Ltd.).

(ii) The enzyme sensors were immersed in the measurement solution A. A potential of 0.2 V was applied to the enzyme sensors. The enzyme sensors were left still until current values in the enzyme sensors were constant. Then the enzyme sensors were immersed in the measurement solution B, and the amount of change in the current values were measured.

(iii) The aforementioned step (ii) was repeated for five times. The amount of change in the current values in the $N^{th}$ time of step (ii) was referred to as the amount of change in the $N^{th}$ time. N is a natural number from 1 to 5.

(iv) A value (hereinafter referred to as $5^{th}/1^{st}$ ratio) was calculated by dividing the amount of change in the $5^{th}$ time by the amount of change in the $1^{st}$ time, and multiplying the result by 100. If the $5^{th}/1^{st}$ ratio was 90% or greater, then the repeat reactivity was evaluated as excellent. If the 5th/$1^{st}$ ratio was 80% or greater and less than 90%, then the repeat reactivity was evaluated as good. If the $5^{th}/1^{st}$ ratio was less than 80%, then the repeat reactivity was evaluated as insufficient. Table 1 shows the results of the evaluation. In Table 1, in the column of "Repeat Reactivity", the mark "⊚" means that the repeat reactivity was excellent; the mark "○" means that the repeat reactivity was good; and the mark "X" means that the repeat reactivity was insufficient.

(3-4) Evaluation of Preservation Stability

The enzyme sensors were stored for 14 days after production in an environment with a temperature of 5° C. and a humidity of 50% RH. After the storage period, the enzyme sensors were attached to the compact potentiostat (miniSTAT100, manufactured by BioDevice Technology, Ltd.) and immersed in the measurement solution A. A potential of 0.2V was applied to the enzyme sensors, and the enzyme sensors were left still until current values in the enzyme sensors were constant. The enzyme sensors were then before storage ratio was less than 80%, the preservation stability was evaluated as insufficient. Table 1 shows the result of the evaluation. In Table 1, in the column of "Preservation Stability", the mark "⊚" means that the preservation stability was excellent; the mark "○" means that the preservation stability was good; and the mark "X" means that the preservation stability was insufficient.

The invention claimed is:

1. An enzyme sensor configured to measure a measurement target substance included in a secretion of a living body, the sensor comprising:
  a layered structure comprising, arranged in the following order: (a) an absorber layer configured to absorb the secretion, (b) an enzyme layer comprising an enzyme, and (c) an electrode part, the absorber layer comprising at least one selected from the group consisting of a photocurable composition and a thermosetting composition, the absorber layer further comprising a polymeric material having a chemically bound crosslinked structure, the polymeric material including at least one of:
    a polymer of polyvinyl alcohol containing an azide group in a side chain;
    a polymer of polysaccharide containing an azide group in a side chain; or
    a polymer of polyvinyl alcohol or polysaccharide, the polymer having a crosslinked structure in which azide groups are crosslinked; and
  a mediator layer between the enzyme layer and the electrode part, the mediator layer including one or more electron transport mediators selected from the group consisting of ferrocene, quinones, ferrocenecarboxylic acid, potassium ferricyanide, osmium complex, ruthenium complex, phenothiazine derivative, phenazine methosulfate derivative, p-aminophenol, meldola blue, and 2,6-dichlorophenolindophenol,
  the mediator layer including (i) a first surface, wherein the enzyme layer is on the first surface and (ii) a second surface, wherein the electrode part is on the second surface, the enzyme sensor further comprising a base material layer configured to support the electrode part, and
the base material layer being made of thermoplastic elastomer.

2. The enzyme sensor according to claim 1, wherein the absorber layer is positioned to be in contact with the living body when the enzyme sensor is in use.

3. The enzyme sensor according to claim 1, wherein the enzyme layer comprises at least one selected from the group consisting of lactic acid oxidizing enzyme and glucose oxidizing enzyme.

4. The enzyme sensor according to claim 1, wherein the enzyme layer produces an electrode-detectable substance from the measurement target substance in the presence of the enzyme.

5. The enzyme sensor according to claim 4, wherein the electrode part is configured to electrically detect an amount or a concentration of the electrode-detectable substance.

6. The enzyme sensor according to claim 1, further comprising an arithmetic unit configured to calculate an amount of the measurement target substance contained in the secretion or a concentration of the measurement target substance contained in the secretion based on a result detected in the electrode part.

7. The enzyme sensor according to claim 1, further comprising a data transmission unit configured to transmit detected data that shows a result detected in the electrode part.

8. An enzyme sensor system comprising:
the enzyme sensor according to claim 7,
a data receiving unit configured to receive the detected data transmitted by the data transmission unit, and
a receiver-side arithmetic unit configured to calculate an amount of the measurement target substance contained in the secretion or a concentration of the measurement target substance contained in the secretion based on the detected data received by the data receiving unit.

9. The enzyme sensor according to claim 1, wherein the enzyme layer includes one of a polymer of polyvinyl alcohol or a polymer of polysaccharide.

10. The enzyme sensor according to claim 9, wherein one of the polymer of polyvinyl alcohol or the polymer of polysaccharide included in the enzyme layer includes an azide group.

* * * * *